United States Patent
Bueno Ramirez et al.

(10) Patent No.: US 10,766,948 B2
(45) Date of Patent: Sep. 8, 2020

(54) MONOCLONAL ANTIBODIES SPECIFIC FOR THE PIII ANTIGEN OF HUMAN ADENOVIRUS (ADV), PRODUCED AND SECRETED BY CELL HYBRIDOMAS, USEFUL FOR DETECTION AND DIAGNOSIS OF ADV INFECTION

(71) Applicant: PONTIFICIA UNIVERSIDAD CATOLICA DE CHILE, Santiago (CL)

(72) Inventors: Susan Marcela Bueno Ramirez, Santiago (CL); Alexis Mikes Kalergis Parra, Santiago (CL); Jorge Eugenio Mora Alarcon, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 0 days.

(21) Appl. No.: 16/070,730

(22) PCT Filed: Jan. 20, 2017

(86) PCT No.: PCT/IB2017/050312
§ 371 (c)(1),
(2) Date: Oct. 24, 2018

(87) PCT Pub. No.: WO2017/125892
PCT Pub. Date: Jul. 27, 2017

(65) Prior Publication Data
US 2019/0048065 A1 Feb. 14, 2019

(30) Foreign Application Priority Data
Jan. 21, 2016 (CL) .................................. 2016-00164

(51) Int. Cl.
*A61K 39/42* (2006.01)
*C07K 16/08* (2006.01)
(Continued)

(52) U.S. Cl.
CPC ...... *C07K 16/081* (2013.01); *G01N 33/54313* (2013.01); *G01N 33/56983* (2013.01)

(58) Field of Classification Search
None
See application file for complete search history.

(56) References Cited

U.S. PATENT DOCUMENTS 4,487,829 A  12/1984 Sharp et al.
6,248,514 B1  6/2001 Hutchins et al.
(Continued)

FOREIGN PATENT DOCUMENTS

WO   2006/119062 A3   11/2006
WO   WO-2008136774 A1 * 11/2008 ....... A61K 39/39558

OTHER PUBLICATIONS

International Search Report and Written Opinion for International Application No. PCT/IB2017/050312 (dated Feb. 12, 2018) (12 Pages).

*Primary Examiner* — M Franco G Salvoza
(74) *Attorney, Agent, or Firm* — Lucas & Mercanti, LLP (57) ABSTRACT

The present invention refers to monoclonal antibodies, or fragments thereof, which recognize the pIII protein of the Adenovirus (ADV), useful for developing diagnostic methods of ADV infection in humans. Particularly, it refers to a monoclonal antibody or fragment thereof comprising a variable region of the heavy chain having a sequence with at least a 90%, 95% or 99% of identity with the SEQ ID No: 1 or SEQ ID No: 5 and a variable region of the light chain having a sequence with at least a 90%, 95% or 99% of identity with the SEQ ID No: 2 or SEQ ID No: 6. It also is (Continued)

addressed to the nucleotide sequences which define said antibodies, in vitro and/or ex vivo diagnostic methods of ADV infection in a biological sample using said monoclonal antibodies, and diagnostic kits for detecting ADV comprising at least one monoclonal antibody against ADV according to the above description.

18 Claims, 4 Drawing Sheets

Specification includes a Sequence Listing.

(51) Int. Cl.
*G01N 33/543* (2006.01)
*G01N 33/569* (2006.01)

(56) References Cited

U.S. PATENT DOCUMENTS

| | | |
|---|---|---|
| 2008/0081047 A1 | 4/2008 | Berry et al. |
| 2011/0206657 A1 | 8/2011 | Zeng |
| 2011/0262892 A1 | 10/2011 | Aoyagi et al. |

* cited by examiner

SEQUENCE LISTING

```
<160> NUMBER OF SEQ ID NOS: 12

<210> SEQ ID NO 1
<211> LENGTH: 203
<212> TYPE: PRT
<213> ORGANISM: Artificial Sequence
<220> FEATURE:
<223> OTHER INFORMATION: Synthetic- Hybridoma 7E11- anti pIII VH

<400> SEQUENCE: 1

Met Glu Cys Ser Trp Val Ile Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
        35                  40                  45

Thr Glu Tyr Thr Met His Trp Val Lys Gln Ser His Gly Gln Ser Leu
    50                  55                  60

Glu Trp Ile Gly Gly Ile Asn Pro Asn Asn Gly Gly Thr Arg Tyr Asn
65                  70                  75                  80

Gln Asn Phe Lys Gly Lys Ala Thr Leu Thr Val Asp Lys Ser Ser Ser
                85                  90                  95

Thr Ala Tyr Met Glu Leu Arg Ser Leu Thr Ser Glu Val Tyr Tyr Cys
            100                 105                 110

Ala Arg Leu Gly Gln Gly Asp Val Tyr Trp Phe Phe Asp Val Trp Gly
        115                 120                 125

Ala Gly Thr Thr Val Thr Val Ser Ser Ala Lys Thr Thr Pro Pro Ser
    130                 135                 140

Val Tyr Pro Leu Ala Leu Lys Thr Leu Gly Glu Phe Phe Phe Gly
145                 150                 155                 160

Trp Gly Gly Gly Gly Gly Ala Asn Pro Pro Leu Arg Gly Pro Ala Pro
```

```
              165                 170                 175
Arg His Arg Arg Thr Ser Thr Arg Pro Leu Val Gln Ser Cys Thr Ile
            180                 185                 190

Ile Asp Phe Arg Cys Gln Ala Ala Glu Leu Met
            195                 200

<210> SEQ ID NO 2
<211> LENGTH: 128
<212> TYPE: PRT
<213> ORGANISM: Artificial Sequence
<220> FEATURE:
<223> OTHER INFORMATION: Synthetic - Hybridoma 7E11 - anti pIII VL

<400> SEQUENCE: 2

Met Glu Ser Asp Thr Leu Leu Leu Trp Val Leu Leu Leu Trp Val Pro
1               5                  10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Leu Thr Arg Ser Glu Gly Gly Pro Ser Trp Lys
        115                 120                 125

<210> SEQ ID NO 3
<211> LENGTH: 612
<212> TYPE: DNA
<213> ORGANISM: Artificial Sequence
<220> FEATURE:
<223> OTHER INFORMATION: Synthetic - Hybridoma 7E11 - anti pIII VH

<400> SEQUENCE: 3
atggaatgca gctgggtcat cctctttctc ctgtcaggaa ctgcaggtgt cctctctgag      60
gtccagctgc aacagtctgg acctgagctg gtgaagcctg ggcttcagt gaagatatcc     120 tgcaagactt ctggatacac attcactgaa tacaccatgc actgggtgaa gcagagccat     180
ggacagagcc ttgagtggat tggaggtatt aatcctaaca tggtggtac taggtacaac     240 cagaacttca gggcaaggc cacattgact gtagacaagt cctccagcac agcctacatg     300
gagctccgca gcctgacatc tgaagtctat tactgtgcaa gactgggaca aggggacgtg     360
tactggttct tcgatgtctg gggcgcaggg accacggtca ccgtctcctc agccaaaacg     420
acacccccat ccgtttatcc cttggccctg aaaactttgg gggaattttt ttttttgggg     480
tggggggggg ggggggggc taacccccc ctacgtggtc ctgcgcccag acatcgaaga     540
accagtacac gtcccttgt ccagtcttgc acaataatag acttcagatg tcaggctgcg     600
gagctcatgt ag                                                        612

<210> SEQ ID NO 4
<211> LENGTH: 387
<212> TYPE: DNA
<213> ORGANISM: Artificial Sequence
```

-continued

```
<220> FEATURE:
<223> OTHER INFORMATION: Synthetic - Hybridoma 7E11 - anti pIII VL

<400> SEQUENCE: 4
atggagtcag acacactgct gttatgggta ctgctgctct gggttccagg ttccactggt     60
gacattgtgc tgacacagtc tcctgcttcc ttagctgtat ctctgggca gagggccacc    120 atctcataca gggccagcaa aagtgtcagt acatctggct atagttatat gcactggaac    180
caacagaaac caggacagcc acccagactc ctcatctatc ttgtatccaa cctagaatct    240
ggggtccctg ccaggttcag tggcagtggg tctgggacag acttcaccct caacatccat    300
cctgtggagg aggaggatgc tgcaacctat tactgtcagc acattaggga gcttacacgt    360
tcggaggggg gaccaagctg gaaataa                                       387

<210> SEQ ID NO 5
<211> LENGTH: 180
<212> TYPE: PRT
<213> ORGANISM: Artificial Sequence
<220> FEATURE:
<223> OTHER INFORMATION: Synthetic - Hybridoma 6F11 - anti pIII VH

<400> SEQUENCE: 5

Met Gln Gln Ser Gly Pro Glu Leu Val Lys Pro Gly Ala Ser Val Lys
1               5                   10                  15

Ile Ser Cys Lys Thr Ser Gly Tyr Thr Phe Thr Glu Tyr Thr Ile His
            20                  25                  30

Trp Val Lys Gln Ser His Gly Lys Ser Leu Glu Trp Ile Gly Gly Ile
        35                  40                  45

Tyr Pro Asn Asn Gly Gly Thr Lys Tyr Asn Gln Lys Phe Lys Gly Lys
    50                  55                  60

Ala Thr Leu Thr Val Asp Lys Ser Ser Ser Thr Ala Tyr Met Glu Leu
65                  70                  75                  80

Arg Ser Leu Thr Ser Glu Asp Ser Ala Val Tyr Tyr Cys Ala Arg Leu
                85                  90                  95

Gly Gln Gly Asp Val His Trp Phe Phe Asp Val Trp Gly Ala Gly Thr
            100                 105                 110

Thr Val Ile Val Ser Ser Ala Lys Thr Thr Pro Pro Ser Val Tyr Pro
        115                 120                 125

Leu Ala Leu Lys Asn Leu Gly Lys Lys Gly Leu Ser Ala Trp Ala Pro
    130                 135                 140

Gly Thr Leu Gly Lys Pro Ile Thr Trp Val Leu Arg Pro Lys His Gln
145                 150                 155                 160

Lys Pro Met His Val Pro Leu Ser His Leu Ala Gln Ile Ile Asp Cys
                165                 170                 175

Lys Ser Ser Met
            180

<210> SEQ ID NO 6
<211> LENGTH: 145
<212> TYPE: PRT
<213> ORGANISM: Artificial Sequence
<220> FEATURE:
<223> OTHER INFORMATION: Synthetic - Hybridoma 6F11 - anti pIII VL

<400> SEQUENCE: 6

Met Val Leu Thr Gln Ser Pro Ala Ser Leu Ala Val Ser Leu Gly Gln
1               5                   10                  15

Arg Ala Thr Ile Ser Tyr Arg Ala Ser Lys Ser Val Ser Thr Ser Gly
```

```
                20                  25                  30
Tyr Ser Tyr Met His Trp Asn Gln Gln Lys Pro Gly Gln Pro Arg
        35                  40                  45

Leu Leu Ile Tyr Leu Val Ser Asn Leu Glu Ser Gly Val Pro Ala Arg
    50                  55                  60

Phe Ser Gly Ser Gly Ser Gly Thr Asp Phe Thr Leu Asn Ile His Pro
65                  70                  75                  80

Val Glu Glu Glu Asp Ala Ala Thr Tyr Tyr Cys Gln His Ile Arg Glu
                85                  90                  95

Leu Thr Arg Ser Glu Gly Gly Pro Ser Trp Lys Arg Ala Asp Ala Ala
            100                 105                 110

Pro Thr Val Ser Ile Phe Pro Pro Tyr Ser Lys Ala Trp Glu Lys Gly
        115                 120                 125

Ala Ala Leu Val Leu Arg Asn Arg Arg Lys Thr Lys Arg Pro Pro Pro
    130                 135                 140

Pro
145

<210> SEQ ID NO 7
<211> LENGTH: 543
<212> TYPE: DNA
<213> ORGANISM: Artificial Sequence
<220> FEATURE:
<223> OTHER INFORMATION: Synthetic - Hybridoma 6F11 - anti pIII VH

<400> SEQUENCE: 7
atgcaacagt ctggacctga gctggtgaag cctggggctt cagtgaagat atcctgcaag      60
acttctggat acacattcac tgaatacacc atacactggg tgaagcagag ccatggaaag     120
agccttgagt ggattggagg tatttatcct aacaatggtg gtactaagta caaccagaag     180
ttcaagggca aggccacatt gactgtagac aagtcttcca gcacagccta catggagctc     240
cgcagcctta catctgagga ttctgcagtc tattattgtg caagactggg acaaggggac     300
gtgcattggt tcttcgatgt ctggggcgca gggaccacgg tcatcgtctc ctcagccaaa     360
acgacacccc catccgttta tcccttggcc ctgaaaaacc ttgggaaaaa aggtttatcc     420
gcctgggccc ctggaacctt gggaaaaccc attacgtggg tcctgcgccc aaacatcaa      480 aaaccaatgc acgtcccctt gtcccatctt gcacaaataa tagactgcaa atcctcaatg     540
taa                                                                  543

<210> SEQ ID NO 8
<211> LENGTH: 438
<212> TYPE: DNA
<213> ORGANISM: Artificial Sequence
<220> FEATURE:
<223> OTHER INFORMATION: Synthetic - Hybridoma 6F11 - anti pIII VL

<400> SEQUENCE: 8
atggtgctga cacagtctcc tgcttcctta gctgtatctc tggggcagag ggccaccatc      60
tcatacaggg ccagcaaaag tgtcagtaca tctggctata gttatatgca ctggaaccaa     120
cagaaaccag acagccacc cagactcctc atctatcttg tatccaacct agaatctggg     180
gtccctgcca ggttcagtgg cagtgggtct gggacagact tcaccctcaa catccatcct     240
gtggaggagg aggatgctgc aacctattac tgtcagcaca ttagggagct tacacgttcg     300
gaggggggac aagctggaa acgggctgat gctgcaccaa ctgtatccat cttcccacca     360
tacagtaaag cttgggaaaa gggggcggca ttggttctga ggaaccggcg taaaaccaaa     420
```

```
aggcccccccc cccttaa                                                         438

<210> SEQ ID NO 9
<211> LENGTH: 33
<212> TYPE: DNA
<213> ORGANISM: Artificial Sequence
<220> FEATURE:
<223> OTHER INFORMATION: Synthetic - nucleotides of primer MuIgkVL5'-B

<400> SEQUENCE: 9
gggaattcat ggagacagac acactcctgc tat                                         33

<210> SEQ ID NO 10
<211> LENGTH: 39
<212> TYPE: DNA
<213> ORGANISM: Artificial Sequence
<220> FEATURE:
<223> OTHER INFORMATION: Synthetic - nucleotides of primer MuIgkVL5' -C

<400> SEQUENCE: 10
actagtcgac atggagwcag acacactsct gytatgggt                                   39

<210> SEQ ID NO 11
<211> LENGTH: 33
<212> TYPE: DNA
<213> ORGANISM: Artificial Sequence
<220> FEATURE:
<223> OTHER INFORMATION: Synthetic - Nucleotides of primer MuIgVH5' - A

<400> SEQUENCE: 11
gggaattcat grasttskgg ytmarctkgr ttt                                         33

<210> SEQ ID NO 12
<211> LENGTH: 35
<212> TYPE: DNA
<213> ORGANISM: Artificial Sequence
<220> FEATURE:
<223> OTHER INFORMATION: Synthetic - Nucleotides of primer MuIgVH5' -F

<400> SEQUENCE: 12
actagtcgac atgaacttyg ggytsagmtt grttt                                       35
```

MONOCLONAL ANTIBODIES SPECIFIC FOR THE PIII ANTIGEN OF HUMAN ADENOVIRUS (ADV), PRODUCED AND SECRETED BY CELL HYBRIDOMAS, USEFUL FOR DETECTION AND DIAGNOSIS OF ADV INFECTION

CROSS REFERENCE TO RELATED APPLICATION

This Application is a 371 of PCT/IB2017/050312 filed on Jan. 20, 2017 which claims the benefit of Chilean Patent Application No. 2016-00164, filed Jan. 21, 2016 which is incorporated herein by reference.

FIELD OF THE INVENTION

The present invention refers to monoclonal antibodies, or fragments thereof, which recognize the Adenovirus (ADV) pIII protein, useful for developing human ADV-infection diagnostic methods.

BACKGROUND OF THE INVENTION

The virus denominated human Adenovirus (ADV) is responsible of producing diverse clinical pictures in the population, which include from conjunctivitis, gastroenteritis to respiratory diseases of all types (such as mild pharyngitis to acute respiratory diseases of the lower respiratory tract, such as pneumonia). Studies have demonstrated that this virus produces a high percentage of morbidity and even the death of infants, military recruits and immunocompromised people worldwide. ADV is known for being a persistent virus remaining latent in previously infected individuals and it can be reactivated by diverse factors, carrying out to the generation a more severe disease. Its genome contains double stranded DNA, which does not have nuclear envelope and codifies for 9 proteins. The capsid that covers it has icosahedron form and it is composed by 3 main proteins: Hexon, Penton (highly conserved) and the fiber. Studies have reported that the penton protein and the fiber are in charge of the attack and entry to the host cell, promoting this last one the internalization of the virus interacting with the receptors in the cell surface. There are more than, 50 serotypes of ADV in humans, which are grouped in 6 species which are subdivided from A-F. Within the subdivision some of the strains—B, C and E—have greater clinic relevance in respiratory diseases, wherein the severity grade of the disease will depend on the age (children <4 years and adults) and the immunologic status of infected patients.

Nowadays the diagnostic and detection of ADV methods performed by the Public Health services include a test based on the viral antigen detection by direct immunofluorescence in swab or nasopharyngeal aspirate samples, polymerase chain reaction (PCR) and cell culture, from a blood sample. Of the mentioned techniques, the viral panel based on immunofluorescence allows to detect a greater number of respiratory virus, being 12 types in the case of Respiratory Viral Panel (RVP) PCR utilizing Luminex xTAG and 14 types for the eSensor Respiratory Viral Panel. Despite to this wide range of detection, is important to note the cost and response time factors used by them (in the case of the first one the cost is approximately USD 60-80 (CLP 42.000-56.000) and a response time between 12 to 18 hours).

Based on the above background, it is fundamental generating and counting with a diagnostic test ex vivo or fast in vitro, effective and low cost for the ADV detection which can compete against the features of the available diagnostic methods. In front of such problem, the monoclonal antibodies of the invention appear as an alternative needed to address said need, since they allow the specific recognition of viral antigens in samples of patients infected with ADV. Currently, there are antibodies used for research (Thermo Scientific Cat. #MS-587) and diagnostic purposes (Abcam® ab6982), however, monoclonal antibodies which specifically recognize the pIII protein of this virus have not been reported.

A monoclonal antibody is a type of homogeneous antibody which is characterized by specifically recognizing a single antigen. They are produced by a single hybrid cell (hybridoma), which is product of the fusion of a B lymphocyte clone and a tumor plasmatic cell. The property of specifically binding and with high affinity to an antigen has driven the development of monoclonal antibodies as a tool of great utility for the detection of molecules which generate a great scientific, clinical interest and of industrial use. Nowadays, the monoclonal antibodies are widely used, in both basic and applied research, due to their specificity and reproducibility, which allow to support the research in better manner. However, it is in the biomedicine area wherein the monoclonal antibodies have had huge practical applications, either for diagnostic and treatment of multiple infectious diseases, and as therapy for other pathologies. While it is true that the monoclonal antibodies are used in all types of detection and diagnostic techniques, it is in the design of kits for in vitro diagnostic wherein the best results have been obtained. For that, there are currently diverse fast detection kits, such as the pregnancy test, which is based on the determination of the chorionic gonadotropin (hCG) levels in the urine using anti hCG antibody. Also, the monoclonal antibodies for therapeutic use have gained great relevance. Currently, there are therapeutic treatments for different pathologies, using commercial monoclonal antibodies such as: Alemtuzumad, Gemtuzumab ozogamicina, Rituximab, Trastumab, among others.

Currently, there are monoclonal antibodies against different proteins of the adenovirus: however, it is highly noted the production of antibodies against the hexon protein and the capside fiber in several published works. A clear example of the above, it is observed in U.S. Pat. No. 4,487,829, wherein they achieve to generate antibodies called anti 2-Hx-2 capable of detecting the hexon antigen in the C subgroup (1,2,5) of human adenovirus. On the other hand, the present application shows the existence of new monoclonal antibodies, or fragments thereof, which recognize the pIII protein of the Adenovirus (ADV).

Additionally, document US20110262892A1 describes detection or virus measurement methods, wherein one of the detected virus is Adenovirus, however, this document does not describe specific monoclonal antibodies or fragments thereof which recognize the Adenovirus pIII protein as the present application does.

Having into account the high production and competitiveness in the market of anti hexon monoclonal antibodies, it is required the search and development of new monoclonal antibodies against conserved and abundant proteins in the virion structure. Such is the case of the monoclonal antibodies of this invention, which are directed against the pIII protein (base penton), a highly conserved protein among ADV subgroups. These are the first monoclonal antibodies produced against this protein, which demonstrated being capable of detecting viral particles from the clinical samples with high sensitivity.

Thus, the present invention comprises products, such as monoclonal antibodies, and an alternative method which uses them for detection and fast, effective and accurate diagnostic in patients infected with ADV with a 100% of specificity in clinical samples and capable of detecting by ELISA, concentrations equivalent 1.5 ng of the specific antigen. This will allow clinical professionals determining in an early manner an appropriate clinical protocol for individuals suffering a respiratory infection caused by this virus.

SUMMARY OF THE INVENTION

Figure 6:
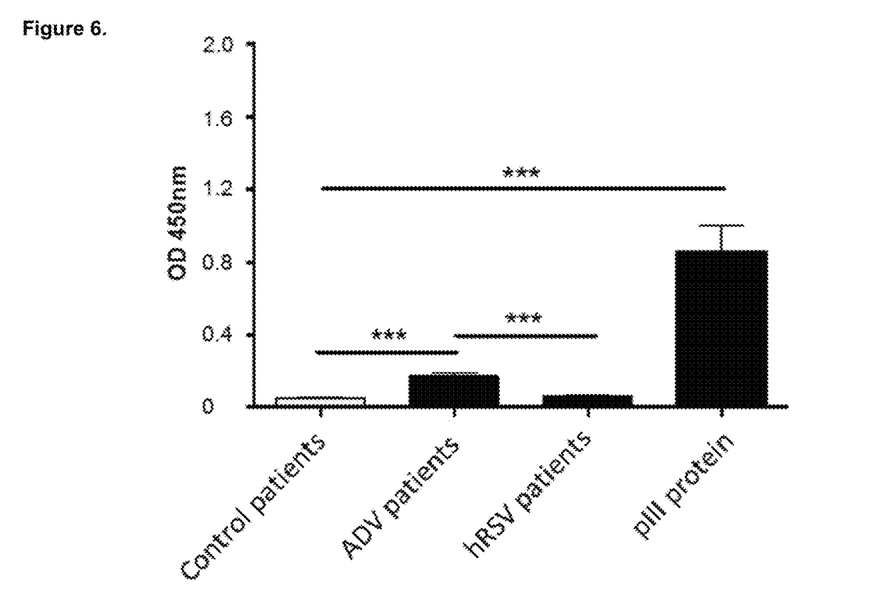

The present invention refers to two monoclonal antibodies against Adenovirus (ADV). Concretely, the present invention involves two murine monoclonal antibodies, secreted by cell lines of hybridomas denominated 7E11 and 6F11, and which react against the pIII ADV antigen. These antibodies do not compete with each other for the binding site to the antigen, nor exert an impediment for simultaneously binding to it. Said monoclonal antibodies can be used for detection assays, diagnostic and/or determination of infection by ADV. These antibodies can be simultaneously used for increasing detection sensitivity in clinical samples wherein an insufficient amount and availability of antigen exists. For example, as it is shown in FIG. 6, antibodies coming from 7E11 are capable to efficiently capture the pIII protein of ADV in clinical samples. These captured and immobilized proteins were detected later by the antibody generated by the 6F11 hybridoma, which was conjugated with an enzyme which acts over a chromogenic substrate. This quality allows the combination of both antibodies with different labels for detecting the same antigen in samples wherein it is found in scarce amount.

The invention provides the opportunity of developing ex vivo or in vitro diagnostic and detection of the pIII viral ADV antigen, in which the monoclonal antibodies produced and secreted by the 7E11 and 6F11 hybridomas are used in assays such as ELISA, fluorescence microscopy and immunoblot. The samples to be analyzed can be: in vitro cells infected with ADV, nasal secretions, nasal washes, pharyngeal secretions and/or bronchial washes or secretions, serum, cerebrospinal fluid, among others. The invention provides the capability of detecting ADV in biological samples and cell cultures, using the monoclonal antibodies produced and/or secreted by the cell lines of the previously mentioned hybridomas, coupled to any type of solid support, such as nitrocellulose, nylon membrane, magnetics spheres, fluorescent spheres or other support, or coupled to any other molecule, such as enzymes, proteins, fluorophores, radioactive isotopes or any other chemical compound. The invent can be used in ADV detection kits, comprising the antibodies produced by the mentioned hybridomas. Also, the present invention comprises within its scope, involving any type of molecule or substrate chemically bond, such as labels, fluorophores, biotin, radioisotopes, metals, enzymes and/or any chemical element coupled to the monoclonal antibodies secreted by the 7E11 and 6F11 hybridomas, wherein said molecule or substrate chemically bound allows visualization or detection the antibody. Thus, the invention also provides antibodies which specifically recognize the pIII protein coupled to molecules, substrates or labels different from the antibody, as part of the detection, analysis and/or diagnostic method in biological samples.

DESCRIPTION OF THE FIGURES

FIG. 1. Detection of ADV pIII protein by the monoclonal antibodies produced by the 7E11 and 6F11 hybridomas, in an indirect ELISA assay. The plate was activated with 50 ng of pIII recombinant protein of purified ADV, or with $1 \times 10^6$ pfu of ADV. As negative controls, other wells with $1 \times 10^6$ pfu of human Respiratory Syncytial Virus (HRSV) or with 50 ng of bovine serum albumin (BSA) protein were activated. Another control wells were also included: without antigen (with primary antibody and HRP-conjugated mouse anti-IgG antibody, denominated in the experiment as "non-activated") and wells without antigen nor primary antibody, only with mouse anti-IgG antibody (HRP). Later, the wells were incubated with the anti-pIII antibodies coming from the 7E11 hybridoma, in an amount of 170 ng (A) and the 6F11 hybridoma in an amount of 170 ng (B). The data shown in the graph express the absorbance detected at 450 nm, emitted by the conversion of the tetramethylbenzidine substrate to a colored compound, catalyzed by the Horseradish peroxidase (HRP) enzyme present in a mouse anti-IgG secondary antibody which was bound specifically to the antibodies secreted by the 7E11 and 6F11 hybridomas. The values correspond to the average +/– the standard deviation of the absorbance emitted by each sample in at least two independent experiments.  $P<0.01$  $P<0.0001$ using one-way ANOVA test compared to the negative control and ascertainment by Dunnett's multiple comparisons; ns, there are no significant difference compared to the negative control.

FIG. 2. Determination of sensitivity of monoclonal antibodies produced by the 7E11 and 6F11 hybridomas in the detection of the pIII protein of ADV. ELISA plates were activated with serial dilutions 1:2 beginning with 50 ng of pIII protein and ending with 0.04 ng (A) and serial dilutions of an inoculum $1 \times 10^5$ pfu of ADV starting from 1:2 to the dilution 1:5120 (B). Wells not activated as negative control were included. The data shown in the graph express the absorbance at 450 nm emitted by the conversion of the tetramethylbenzidine substrate to a colored compound catalyzed by the Horseradish peroxidase (HRP) enzyme present in the anti-pIII antibodies coming from the 7E11 and 6F11 in an amount of 170 ng (A and B). The values correspond to the average of the absorbance emitted by each sample in at least two independent experiments.

FIG. 4. Confirmation of specificity of monoclonal antibodies secreted by the 7E11 and 6F11 hybridomas, using dot blot. The anti-pIII antibodies of ADV produced by the 7E11 and 6F11 hybridomas were incubated for 1 hour with a nitrocellulose membrane which contained the following immobilized samples (in stains form or "dots"): HRSV ($1 \times 10^8$ pfu), ADV ($1 \times 10^6$ pfu), BSA (1 µg), pIII protein of ADV (1 µg, 500 ng y 50 ng), and 20 µg extract of non-infected and infected with ADV A549 cells. After the incubation, the membrane was washed and incubated for 1 hour with a mouse anti-IgG secondary antibody conjugated with the HRP protein. After the incubation, the visualization of the monoclonal antibodies binding to the antigen was performed by the capture of the chemiluminescence produced by the catalysis of the commercial substrate "enhanced chemiluminescence Western blot detection system" (ECL, Amersham, Uppsala, Sweden). It is observed that the antibodies produced by the 7E11 and 6F11 hybridomas are only bound to the "dots", wherein the pIII protein of ADV is found present, the ADV virus and infected with ADV cells, confirming the specificity of these antibodies.

FIG. 5. Detection of the pIII protein of ADV by immunofluorescence in A549 cells infected with ADV. A549 cells were grown in vitro until reaching a confluence of 70-90%, for infection for 48 hours with ADV. Later, these cells were fixed with paraformaldehyde and prepared for indirect immunofluorescence. For that a monoclonal primary antibody derived from the 7E11 hybridoma or of the 6F11 hybridoma was used, also an anti-ADV (Abcam) commercial antibody. As secondary antibody a mouse anti-IgG commercial antibody conjugated to the Alexa Fluor 488 fluorophore or a rabbit anti-IgG conjugated with the same fluorophore was used, which emits fluorescence at 519 nm (intense signal). The cell nuclei were dyed with the TOPRO-3 iodide fluorophore, which emits fluorescence at 661 nm (filled circles). It is observed a strong reactivity in the cytoplasm (white arrows) only in infected cells when any of the two primary antibodies is used.

FIG. 6. Detection of ADV in clinical samples by Sandwich ELISA, using the combination of the monoclonal antibodies secreted by the 7E11 and 6F11 hybridomas. ELISA plates were activated with 170 ng of antibody secreted by the 7E11 hybridoma, working as capture antibody. The wells activated with the capture antibody were incubated with 50 µl of nasopharyngeal swab (HNF) samples of patients which presented viral respiratory conditions. As negative controls 10 samples of control patients (negative for respiratory virus) were analyzed. 20 samples of positive patients for ADV were used and as specificity control, 20 samples of positive patients for the RSV were included. As positive control, wells to which pIII protein of purified ADV was added, were included. For detection of the protein captured by the 7E11 antibody, the antibodies produced by the 6F11 hybridoma, conjugated to the HRP enzyme were used, in a dilution 1:2000 (75 ng per well). The showed data are the average +/− the standard deviation of the absorbance value emitted at 450 nm of each sample (**$P<0.001$, using one-way ANOVA test compared with positive patients for HRSV or healthy patients).

DETAILED DESCRIPTION OF THE INVENTION

The present invention refers to two monoclonal antibodies, or fragments thereof, of IgG1 isotype, which specifically recognize the pIII protein (also denominated herein as anti-pIII antibodies), of the Adenovirus (ADV). These antibodies are produced by the 7E11 and 6F11 hybridomas. The amino acids sequences of the variable regions of both antibody chains produced by the 7E11 hybridoma are described in SEQ ID No: 1 for the heavy chain and SEQ ID No: 2 for the light chain. The nucleotide sequences which codify them are described in SEQ ID No: 3 and SEQ ID No: 4, respectively. In the same way, the amino acid sequences of the variable regions of both chains of the antibody produced by the 6F11 hybridoma are described in the SEQ ID No: 5 for the heavy chain and SEQ ID No: 6 for the light chain. The nucleotide sequences which codify them are described in the SEQ ID No: 7 and SEQ ID No: 8, respectively.

From these variable sequences, chimeric antibodies comprising them are constructed, including either only one of the variable regions, or mixing them in all the possible combinations. All of these embodiments are found within the scope of the present invention. Namely, the present invention includes antibodies comprising at least one of the sequences SEQ ID No: 1, SEQ ID No: 2. SEQ ID No: 5 and SEQ ID No: 6 and similar sequences with up to 90%, 95% or 99% of homology or identity compared to any of said amino acids sequences. As well as the nucleotide sequences comprising at least one of the sequences SEQ ID No: 3, SEQ ID No: 4, SEQ ID No: 7 and SEQ ID No: 8; as well as their complementary reverse and similar sequences with up to 80%, 85%, 90%, 95% and 99% of homology or identity compared to any of said nucleotide sequences. The highest degree of homology considered in the nucleotide sequences is based on the degeneration of the genetic code. Thus, the present invention also includes a set of nucleotide sequences which codify for a monoclonal antibody, or fragment thereof, which specifically recognize the pIII protein if ADV.

In a specific embodiment of the invention, said antibodies or fragments thereof are conjugated with a label which allows their detection, such as, biotin, metals, enzymes, proteins, fluorophores, radioactive isotopes or any other chemical compound.

Figure 1:
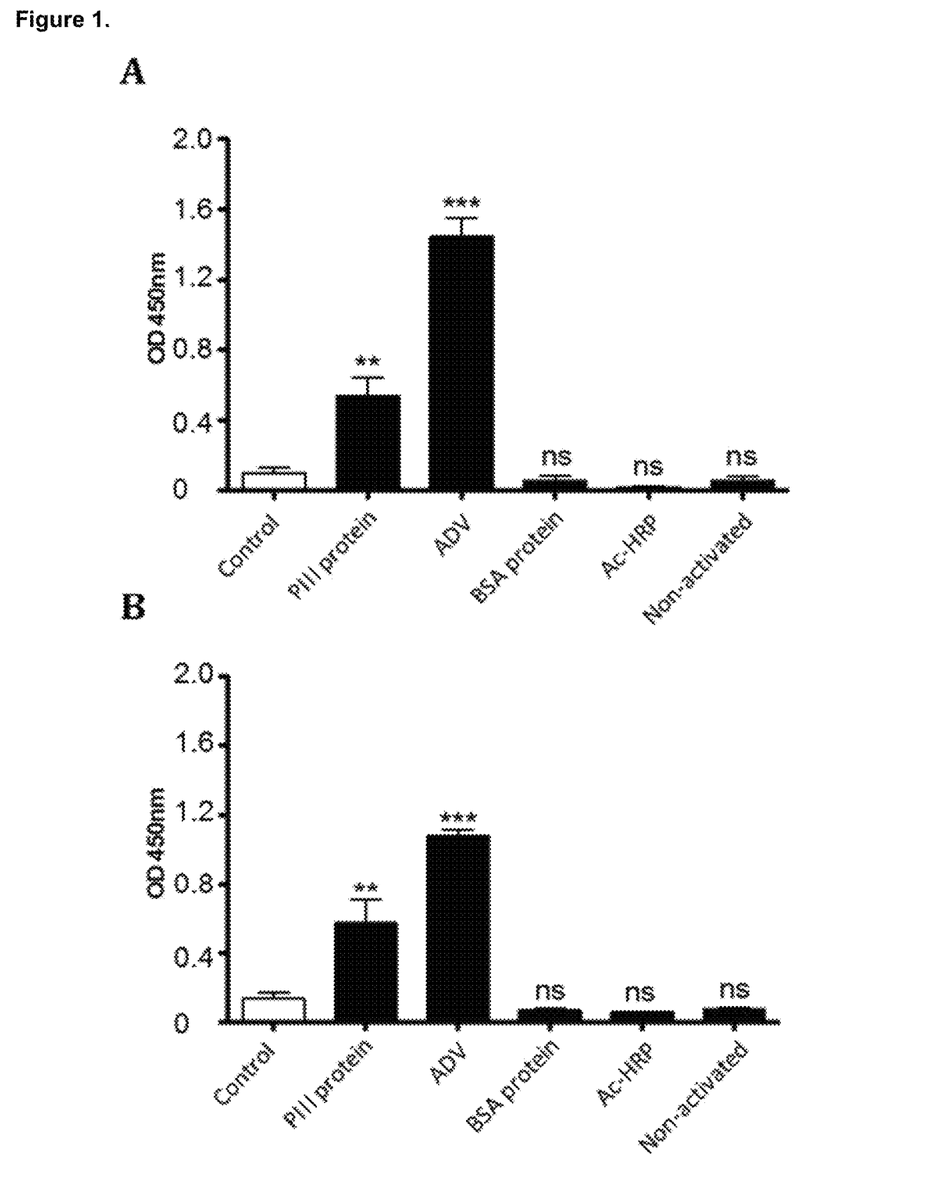
Figure 4:
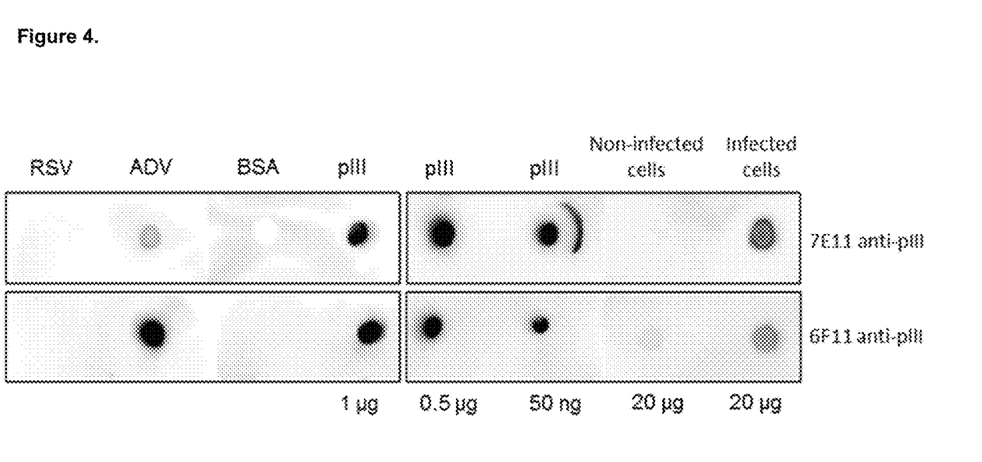

As it is shown in FIGS. 1 and 4, these antibodies do not react with other proteins or molecules present in related viruses or samples of patients with other viruses associated to respiratory infections. This notably decreases the possibility of false negatives when using them in diagnostic methods.

The invention also provides ex vivo or in vitro diagnostic methods and detection of the pIII viral ADV antigen in a biological sample, in which the monoclonal antibodies produced and secreted by the 7E11 and 6F11 hybridomas are used in assays for detection of antibody binding to the antigen.

The method comprises contacting a biological sample selected from: in vitro cells infected with ADV, nasal secretions, nasal washes, cerebrospinal fluid, pharyngeal secretions and/or bronchial washes or secretions, among other, with the monoclonal antibody against ADV or a fragment thereof secreted by the 7E11 and 6F11, and then detecting the binding of the antibody with the antigen with an assay selected from: ELISA, immunoblot, immunofluorescence, immunohistochemistry, immunohistochemistry, flow cytometry, cell sorter, immunoprecipitation and/or Western blot.

Also, the method of the present invention comprises antibodies or fragments thereof produced and/or secreted by the cell lines of the hybridomas mentioned above, coupled to any type of solid support, such as nitrocellulose, nylon membrane, magnetics spheres, fluorescent spheres or other support. In another specific embodiment of the invention, the antibodies or fragments thereof used in the method are conjugated with a label which allows their detection, such as biotin, metals, enzymes, proteins, fluorophores, radioactive isotopes or any other chemical compound.

The invention also describes a detection kit for ADV, which comprises at least one antibody produced by the mentioned hybridomas. In a specific embodiment of the invention, the antibodies or fragments thereof produced and/or secreted by the cell lines of the hybridomas above mentioned used in said kits, are coupled with any type of solid support, such as nitrocellulose, nylon membrane, magnetics spheres, fluorescent spheres or another support. Also, in a specific embodiment of the invention, the antibodies or fragments thereof used un the kit are conjugated with a label which allows their detection, such as biotin, metals, enzymes, proteins, fluorophores, radioactive isotopes or any other chemical compound.

In another specific embodiment of the invention, the diagnostic kit corresponds to an immunochromatographic assay, luminex, flow cytometry, immunofluorescence, radioimmunoassay, Western blot, Dot plot, ELISA, immunodiffusion or immunoprecipitation.

Thus, the invention also provides antibodies which specifically recognize the pIII protein coupled to molecules or substrates or labels different from the antibody, as part of the detection method, analysis and/or diagnostic in biological samples.

EXAMPLES OF APPLICATION

Following, examples which allow demonstrating the different applications of the monoclonal antibodies of the invention are described.

Example 1: Determination of the Nucleotide Sequence which Codifies the Light (VL) and Heavy (VH) Chains of the Variable Region of the ADV Anti-pIII Antibody Secreted by the 7E11 Hybridoma and the ADV Anti-pIII Antibody Secreted by the Hybridoma 6F11

The following protocol was used for the 7E11 and 6F11 hybridomas separately. The hybridoma was grown in culture medium DMEM-high glucose supplemented with 3.7 g/L Sodium Bicarbonate and 10% bovine fetal serum, at 37° C. with 10% $CO_2$, until reaching a cell density of 700,000 cells/ml. The total RNA of $3.5 \times 10^8$ cells was obtained, performing a treatment with Trizol compound (Invitrogen). 0.5 µ/g of RNA was used for generating the cDNA by reaction of retrotranscription with the Impron II kit (Promega). The variable region of the genes which codify the kappa and lambda chains of the immunoglobulins was amplified by PCR. For that, the universal primers of the Ig kit First set of Novagen (catalogue n° 69831-3) were used and the manufacturer instructions were followed. The variable region of the light chain was amplified with the MulgKVL5'-B primers: 5'GGGAATTCATGGAGACAGACA-CACTCCTGCTAT 3' (SEQ ID NO: 9) and MulgKVL5'-C: 5'ACTAGTCGACATGGAGWCAGACACACTSCT-GYTATGGGT3' (SEQ ID NO: 10) and the heavy chain was amplified with the MulgVH5'-A primers: 5'GGGAATTCAT-GRASTTSKGGYTMARCTKGRTTT3' (SEQ ID NO: 11) and MulgVH5'-F: 5'ACTAGTCGACATGAACTTYGGG-YTSAGMTTGRTTT3' (SEQ ID NO: 12). The PCR products were cloned in the pTOPO-TA cloning vector (Invitrogen) according to the manufacturer instructions and sequenced by the sequencing service of the Pontificia Universidad Catolica de Chile in an Abl prism 3130xl sequencer (Applied Biosystem). The deducted amino acid sequences (SEQ ID NO: 1 and SEQ ID NO: 2 for the 7E11 hybndoma and SEQ ID NO: 5 and SEQ ID NO: 6 for the 6F11 hybridoma) were obtained using the Vector NTI bioinformatic software (Invitrogen).

Example 2. ADV Antigens Detection Assay, Determination of Specificity of the Anti-pIII Monoclonal Antibodies of ADV for Purified Antigens of ADV by the Indirect ELISA Assay This assay has as objective demonstrating the specificity by the pIII protein of ADV of the antibodies produced by the 7E11 and 6F11 hybridomas. The detection of the antigen was carried out by the indirect ELISA technique, wherein the ELISA plate was activated with 50 ng of purified antigen for 1 hour at 37° C. In the same way, the plate was activated with $1 \times 10^6$ plaque forming units (PFU) of ADV. As negative controls human Respiratory Syncytial Virus (HRSV) was included under the same conditions in which the ADV was incubated, and also 50 ng of BSA protein were included in an independent well. Later, the plate was washed twice with phosphate-buffered saline (PBS)/Tween 0.05%. Then, the plate was blocked for 2 hours at 37° C. with PBS/FBS 10%. Later, the washes were repeated and then each one of the antibodies (7E11 and 6F11) was incubated to a final concentration of 3.4 µg/ml, diluted in PBS/FBS 10%, for 1 hour at room temperature (each antibody in an independent plate). Commercial antibody control was not used, since monoclonal or polyclonal antibodies against the pIII protein have not been found in the market. After the incubation time, the washes were repeated and to each one of the wells a mouse anti-IgG secondary antibody was added, labeled with horseradish peroxidase enzyme (Horseradish peroxidase, HRP) in dilution 1 in 2,000 (25 ng per well) in PBS/FBS 10%, for 1 hour at room temperature. Finally, washes were performed and it was revealed with 50 µl of citrate buffer/Tetramethylbenzidine (TMB, 3-3'-5-5'tetramethylbenzidine, 1 mg/ml, Becton Dickinson). To stop the reaction, 50 µl of $H_2SO_4$ 2N were added and the result was read in an ELISA lector, at 450 nm. For determining that the reaction of the secondary antibody was specific in recognizing the primary antibody and also that the obtained signal was not caused by an unspecific binding of the secondary antibody to the viral antibody, controls were performed in which only the secondary antibody without primary antibody nor sample (inactivated well) was used. Another control for determining that the reaction of the primary antibody is specific for the antigen, consisted in the use of the antibodies on an ELISA plate which has not been activated with the antigen (without antigen) or using the antibodies on an ELISA plate previously activated with 50 ng of the BSA protein or a different virus (HRSV). The results show that the monoclonal antibodies of the invention are capable of recognizing 50 ng of purified antigen, in a specific manner, since they do not recognize the BSA protein, nor proteins of another related virus (FIGS. 1A and 1B).

Figure 2:
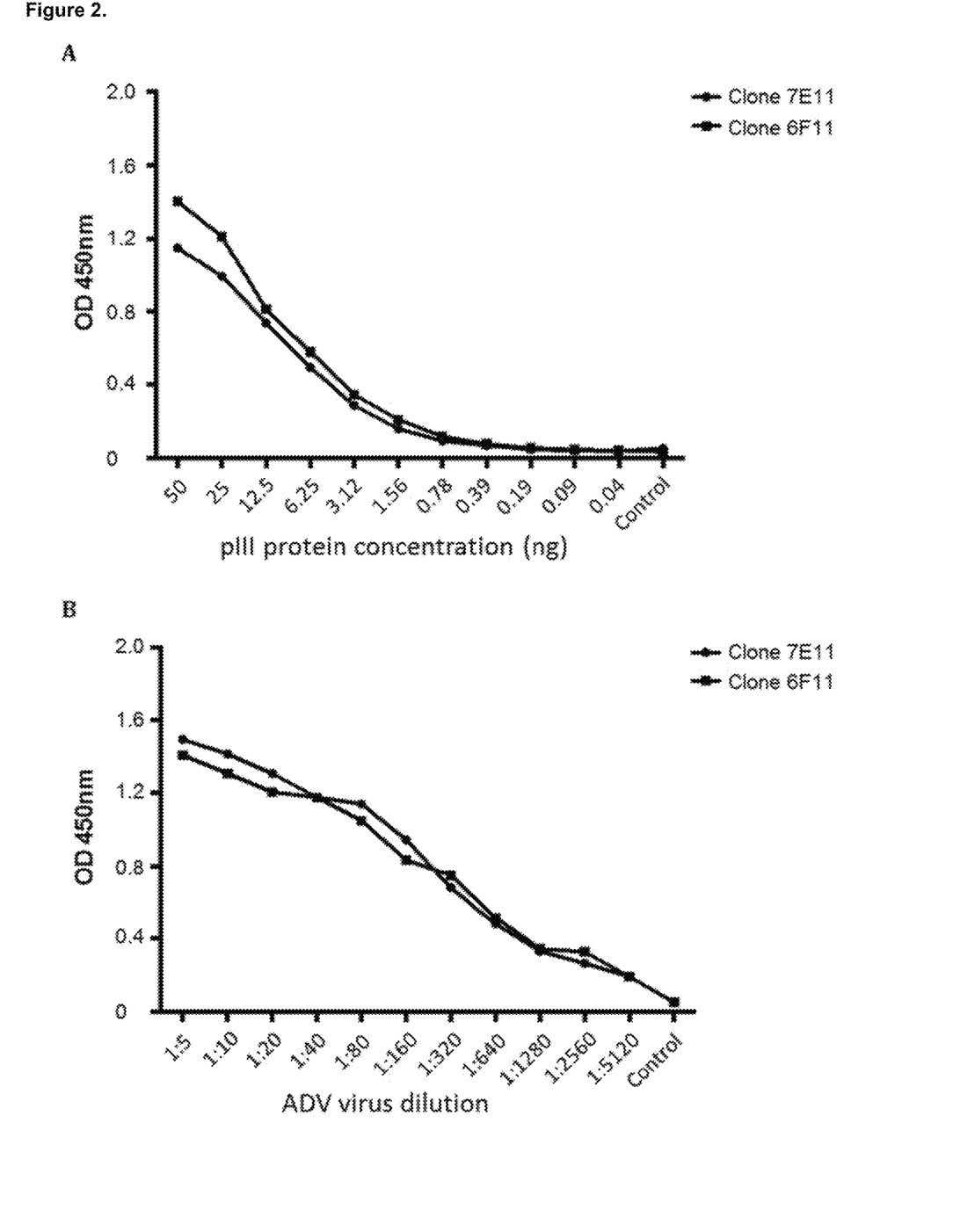

Example 3. Assay for Determining the Sensitivity of the Monoclonal Antibodies for Detection of Viral Antigens The assay was performed for determining the maximum dilution of protein and virus that the anti-pIII monoclonal antibody of ADV coming from the 7E11 and 6F11 hybridomas are capable of detecting by indirect ELISA. For that, the same technique described in the example 2 was used. The plate was activated with 11 serial dilutions 1:2 of pIII protein of ADV, starting with 50 ng of purified antigen. Regarding to the virus, the plate was activated with serial dilutions of 1:2, from $1 \times 10^5$ pfu of virus. The 7E11 or 6F11 anti-pIII antibodies were used in a concentration of 3.4 µg/ml (170 ng/well), diluted in PBS/FBS 10%. Later, the mouse anti-IgG detection antibody in a dilution of 1:2,000 (25 ng/well) was added. The results showed that the 7E11 anti-pIII antibody is capable of recognizing up to 1.56 nanograms (ng) of the pIII protein of ADV. The anti-pIII antibody coming from the 6F11 hybridoma, was capable of detecting until 3.12 ng of pIII ADV protein (FIG. 2A).

Regarding to the sensitivity of the antibodies represented in its capability of detecting the ADV at high dilutions, it can be observed that the anti-pIII antibodies coming from the 7E11 hybridoma can detect all the performed dilutions of the virus, in the same way that the antibody coming from the 6F11 hybridoma, which would be equivalent to 390 viral particles approximately. The two monoclonal antibodies would be efficient and sensitive in the detection of the virus, knowing that it does not exist any commercial antibody until now for detecting the pIII protein (FIG. 2B).

In all the assays, controls which allow to discard unspecific reactions of the antibodies were included, which contained all the components of the assay excepting the sample (pIII protein or ADV virus).

Figure 3:
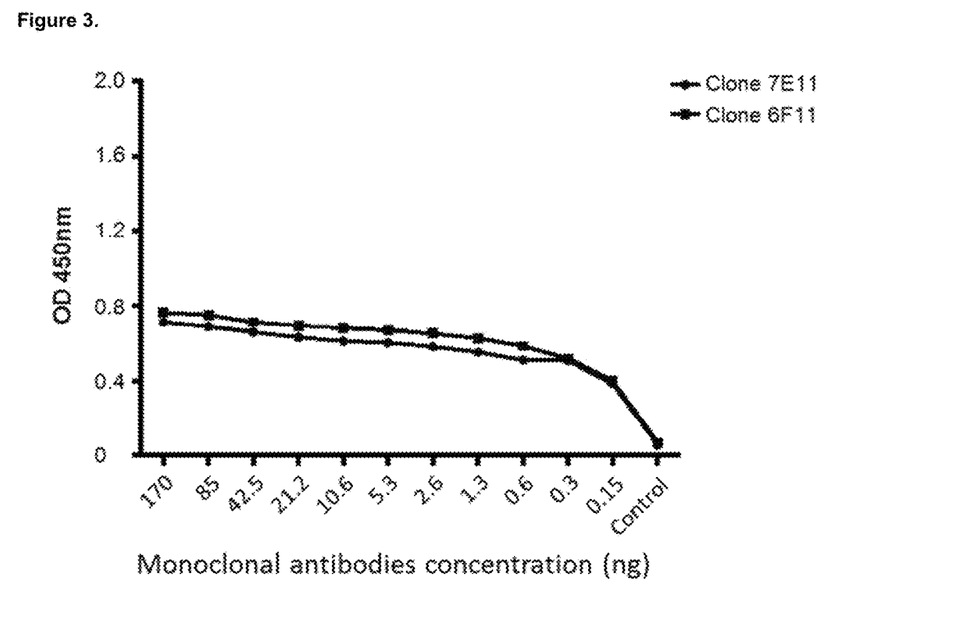
FIG. 3. Serial dilutions assay of the anti-pIII monoclonal antibodies of ADV produced by the 7E11 and 6F11 hybridomas, for detection of purified antigens of ADV. ELISA plates were activated with 50 ng of pIII recombinant protein of ADV and the antigen with serial dilutions 1:2 of the 7E11 or 6F11 anti-pIII antibodies, starting from a concentration of 3.4 µg/ml (170 ng). The data are expressed as the average of the value of the absorbance emitted at 450 nm of each sample in duplicate, in at least two independent experiments.

Example 4. Assay for Determining the Efficiency of the Monoclonal Antibodies for Detecting Viral Antigens The assay was performed for determining the maximum dilution of the anti-pIII monoclonal antibodies of ADV coming from the 7E11 and 6F11 hybridomas, which allow the detection of the viral antigen. For this, the same indirect ELISA technique from the example 2 was used. The plate was activated with 50 ng of purified antigen and the 7E11 or 6F11 anti-pIII antibodies were used performing 11 dilutions 1:2 starting with a concentration of 3.4 µg/ml, using a solution of PBS/FBS 10% as diluent. In FIG. 3 it is observed that for all of the dilutions used in the assay, the 7E11 and 6F11 anti-pIII antibodies are capable of detecting the pIII protein of ADV.

The negative control included in this assay, corresponds to a well which does not contain a sample (pIII protein), was blocked with PBS/FBS 10%, primary antibody (anti-pIII 7E11 or anti-pIII 6F1) and it only contains mouse anti-IgG antibody conjugated with HRP.

Example 5. Clinical Diagnostic of Samples of Patients Infected with ADV, Using Anti-pIII Monoclonal Antibody of ADV by Sandwich ELISA Technique Due to that the availability and concentration of viral proteins in clinical samples obtained from nasopharyngeal swabs is low, it was necessary to modify the detection method and using the sandwich ELISA method, using as capture antibody the anti-pIII antibody coming from the 7E11 hybridoma and as detection antibody the 6F11 anti-pIII clone, conjugated with HRP. For the assay, wells of an ELISA plate were activated with 3.4 µg/ml (170 ng/well) of the anti-pIII antibody coming from the 7E11 hybridoma, diluted in PBS, during 1 hour at 37° C. 2 washes with 0.05% Tween 20 PBS were performed and later the plate was blocked with 200 µL of PBS/10% FBS for 2 hours at 37° C. It was washed again and it was incubated overnight at 4° C. each well with 50 µL of nasopharyngeal aspirates of patients positive for ADV according to the diagnostic method "-D$^3$ Ultra DFA Respiratory Virus Screening and ID Kit de DHI (Diagnostics Hibryds) USA", routinely called "viral panel", and which were treated as described lately*. The following controls were included: 1) control of specificity (50 µL of samples of patients diagnosed with HRSV by the viral panel), 2) positive control (50 ng of pIII recombinant protein of ADV) and 3) negative control corresponding to samples of healthy patients (negative for virus by the viral panel). The next day the washes were performed and each well was incubated for 1 hour at room temperature with 50 µL of the anti-pIII antibody coming from the 6F11 hybridoma conjugated with HRP. The plate was washed 2 more times and it was revealed with 50 µL of TMB solution, it was incubated from 10 to 15 minutes in the darkness. The reaction was stopped with 50 µL of $H_2SO_4$ 2N. The reading of the plate was performed in an Epoch ELISA plate reader, certified for clinical diagnostic. The obtained results for this assay are shown in FIG. 6, wherein it can be observed that the sandwich ELISA technique using the antibody coming from the 7E11 hybridoma as capture antibody and the antibody coming from the 6F11-HRP hybridoma as detection antibody, allows detecting the antigen in samples of patients infected with ADV, which were previously confirmed by direct immunofluorescence in a certified clinical laboratory using the viral panel. The number of patients included in the assay was 20, 17 of which were detected as positive by ELISA with an optical density (OD) above 0.1. This assay demonstrates also the versatility which present the antibodies coming from the 7E11 and 6F11 hybridomas, since they both are capable of binding simultaneously to the antigen without competing nor interfering each other, allowing the capture and later detection of the pIII protein in samples of patients. Also, the figure shows that the produced antibodies are specific since they do not recognize cells of patients infected with other viruses (HRSV).

*: Treatment of Clinical Samples.

The samples used for the assays were obtained from nasopharyngeal swabs contained in universal carrying media, from the Medical Research Center of the Pontificia Universidad Catblica de Chile. The samples were centrifuged at 2.000 rpm for 10 minutes at 4° C. Later, the supernatant (SN1) was separated from the pellet; this latter was incubated with 100 µL of Buffer RIPA (50 mM Tris-HCl pH 8.0, 150 mM NaCl, 1% NP-40, 0.5% Sodium Deoxycholate, 0.1%. SDS and a protease inhibitor cocktail) during 15 minutes at 4° C., Vortex stirring every 5 minutes. Subsequently, it was centrifuged at 2,000 rpm for 10 minutes at 4° C. When finished the obtained supernatant (SN2) was took and it was mixed with the SN1.

Figure 5:
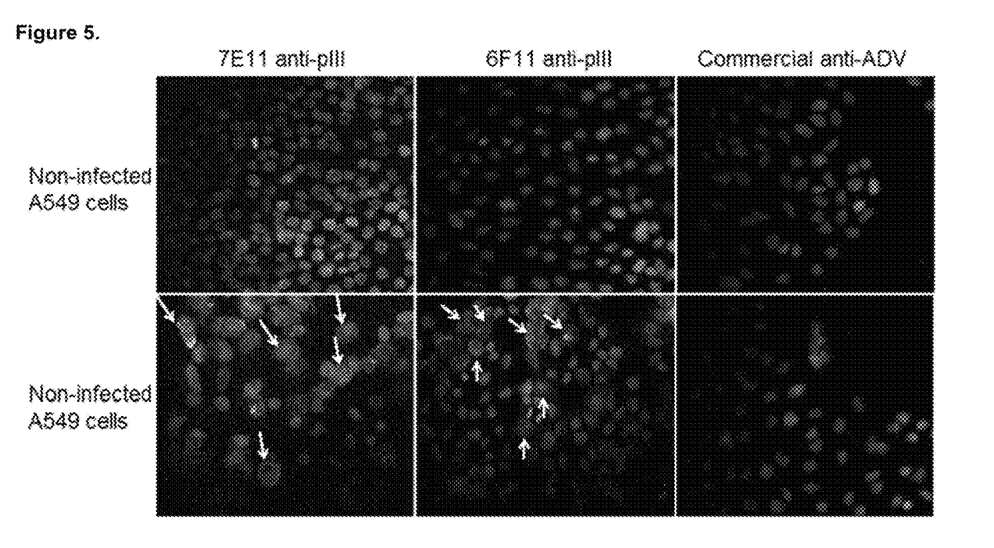

Example 6. Detection of Infection by ADV in A549 Cells by Immunofluorescence, Using ADV Anti-pIII Monoclonal Antibodies This assay was performed for amplifying the spectrum of techniques which allow detecting infection by ADV, using the described invention. An assay was carried out by fluorescence microscopy, wherein infected or non-infected with ADV A549 cells were incubated with the anti-pIII monoclonal antibodies of ADV derived from the hybridomas 7E11 or 6F11, in addition of the anti-ADV commercial polyclonal antibody (Abcam, #ab1039). The protocol used was the following: the cells were fixed with the 4% paraformaldehyde diluted in PBS, for 10 minutes at 25° C. Then, the cells were washed with PBS and they were permeabilized with saponin 0.2% diluted in PBS/FBS 10% for 30 minutes at 25° C. The monoclonal antibodies derived from the 7E11 or 6F11 hybridomas were added and the commercial anti-ADV at a concentration of 3.4 µg/ml, diluted in PBS/FBS 10% for 1 hour at 25° C. Two washes with PBS were performed later and the mouse anti-IgG secondary antibody conjugated with the Alexa fluor 488 (Life Technologies) fluorophore was added, and rabbit anti-IgG secondary antibody, conjugated with the Alexa fluor 488 (ThermoFisher) fluorophore, for detecting the anti-ADV polyclonal antibody, in a dilution 1 in 200 in PBS/FBS 10% for 1 hour at 25° C., in darkness. The washes were repeated and the cores were dyed with TOPRO-3 iodide 642/661 (Invitrogen, #T3605) at a dilution 1:5,000 for 15 minutes at 25° C., in darkness. At last, it was washed with PBS and the assembly of the coverslip was performed for its later observation in an epifluorescence microscopy. The obtained results show that the antibodies constituent of the invention are also useful for specifically recognizing infected cells by immunofluorescence, without binding in unspecific manner to non-infected cells (FIG. 5).

Example 7. Assay of Specificity of the ADV Anti-pIII Monoclonal Antibodies for Purified Antigens of ADV, Using the Dot-Blot Assay This assay has as objective confirming the specificity for the pIII protein of ADV by the antibodies produced by the 7E11 and 6F11 hybridomas, using the immunoblot methodology. The detection of the antigen was carried out by the dot-blot technique, wherein a nitrocellulose membrane is used as solid support for immobilizing the antigen present in a suspended drop. For that, it was deposited over the nitrocellulose membrane 2 μL which each one contained: 1×10 pfu of HRSV, 1×10$^a$ pfu ADV, pIII protein of purified ADV (lpg, 500 ng and 50 ng), 20 μg of A549 cells extract infected with ADV and 20 μg of non-infected A549 cells extract. As negative control. 1 μg of BSA was applied, contained in 2 μL. It was allowed that the solutions applied over the membranes were air dried for 15 minutes. Lately, the membrane was blocked with BSA at 5% in PBS containing Tween-20 0.05%, for 1 h at 25° C. Then, the excess of the antibody non-adhered to antigen was removed performing three washed with PBS-Tween-20 0.05% at 25° C.

The detection of the antibodies bond to antigen was performed by a mouse anti-IgG antibody conjugated to HRP (Invitrogen, Life Technologies #62-6520), which was diluted in blocking solution for 1 h at 25° C., for lately removing the excess of unbound antibody by three washes with PBS-Tween-20 0.05% a 25° C. The visualization of the binding of the monoclonal antibodies to the antigen was performed by the capture of the chemiluminescence produced by the catalysis of the commercial substrate "enhanced chemiluminescence Western blot detection system" (ECL, Amersham, Uppsala, Sweden), mediated by the HRP enzyme bound to the mouse anti-IgG antibody. The capture of the chemiluminescence was performed with the photodocumentation system MyECL (Thermo Fisher). As it is observed in FIG. 4, the antibodies coming from the 7E11 and 6F11 hybridomas only bind to the "dots" containing ADV, pIII protein or cells infected with ADV, and they do not bind in an unspecific manner to the "dots2 containing non-related protein, other viruses or non-infected cells.

The examples described in this specification demonstrate the specificity, efficiency, sensitivity and versatility that these ADV anti-pIII monoclonal antibodies secreted by the cell lines of the 7E11 and 6F11 hybridomas have. The examples herein presented constitute a demonstration of some of the uses of the ADV anti-pIII monoclonal antibodies, but in no way they limit the scope of the present invention.

The invention claimed is:

1. A monoclonal antibody, or a fragment thereof, which binds to the pIII protein of Adenovirus (ADV), comprising a variable region of the heavy chain having a sequence with at least 90%, 95% or 99% identity with SEQ ID NO: 1 or SEQ ID NO: 5 and a variable region of the light chain having a sequence with at least 90%, 95% or 99% identity with SEQ ID NO: 2 or SEQ ID NO: 6.

2. The monoclonal antibody or fragment thereof, according to claim 1, wherein the antibody or fragment thereof is also bound to a label selected from the group consisting of fluorophores, biotin, radioisotopes, metals, proteins and enzymes.

3. A set of nucleotide sequences codifying a monoclonal antibody or a fragment thereof according to claim 1, comprising a sequence with at least 80%, 85%, 90%, 95% or 99% identity with SEQ ID NO: 3 or SEQ ID NO: 7, and their reverse complements, which codifies the variable region of the heavy chain of the antibody, and comprising a sequence with at least 80%, 85%, 90%, 95% or 99% identity with SEQ ID NO: 4 or SEQ ID NO: 8, and their reverse complements, which codifies the variable region of the light chain of the antibody.

4. An in vitro and/or ex vivo ADV infection diagnostic method of a biological sample, wherein the method comprises contacting the biological sample with the monoclonal antibody against ADV or a fragment thereof according to claim 1 and detecting the binding of the antibody to the antigen.

5. The in vitro and/or ex vivo diagnostic method according to claim 4, wherein the biological sample is selected from the group consisting of in vitro cells infected with ADV, nasal secretions, nasal washes, cerebrospinal fluid, pharyngeal secretions and/or bronchial washes or secretions.

6. The in vitro and/or ex vivo diagnostic method according to claim 4, wherein the technique used for the detection of the antibody with the antigen is selected from: ELISA, immunofluorescence, immunohistochemistry, immunochromatography, flow cytometry, cell sorter, immunoprecipitation and/or Western blot.

7. The in vitro and/or ex vivo diagnostic method according to claim 4, wherein the antibody or fragment thereof, is conjugated with a label which allows its detection.

8. The in vitro and/or ex vivo diagnostic method according to claim 7, wherein the antibody is bound to a label selected from the group consisting of biotin, metals, enzymes, proteins, fluorophores and radioactive isotopes.

9. The in vitro and/or ex vivo diagnostic method according to claim 7, wherein the antibody is attached to a solid support.

10. The in vitro and/or ex vivo diagnostic method according to claim 9, wherein the solid support is nitrocellulose, nylon membrane, magnetic spheres, or fluorescent spheres.

11. A diagnostic kit for detecting ADV comprising at least one monoclonal antibody against ADV, according to claim 1.

12. The diagnostic kit according to claim 11, wherein the antibody is attached to a solid support.

13. The diagnostic kit according to claim 12, wherein the solid support is nitrocellulose, nylon membrane, magnetic spheres, or fluorescent spheres.

14. The diagnostic kit according to claim 11, which corresponds to an immunochromatographic, multiplexed nucleic acid assay, flow cytometry, immunofluorescence, radioimmunoassay, Western blot, dot blot, ELISA, immunodiffusion or immunoprecipitation test for detecting ADV.

15. An in vitro and/or ex vivo ADV infection diagnostic method of a biological sample, wherein the method comprises contacting the biological sample with the monoclonal antibody against ADV or a fragment thereof according to claim 2 and detecting the binding of the antibody to the antigen.

16. A diagnostic kit for detecting ADV comprising at least one monoclonal antibody against ADV, according to claim 2.

17. The diagnostic kit according to claim 12, which corresponds to an immunochromatographic, multiplexed nucleic acid assay, flow cytometry, immunofluorescence, radioimmunoassay, Western blot, dot blot, ELISA, immunodiffusion or immunoprecipitation test for detecting ADV.

18. The diagnostic kit according to claim 13, which corresponds to an immunochromatographic, multiplexed nucleic acid assay, flow cytometry, immunofluorescence, radioimmunoassay, Western blot, dot blot, ELISA, immunodiffusion or immunoprecipitation test for detecting ADV.

* * * * *